United States Patent [19]

Wurster et al.

[11] Patent Number: 5,005,579

[45] Date of Patent: Apr. 9, 1991

[54] APPARATUS FOR SPATIAL LOCATION AND DESTRUCTION OF OBJECTS INSIDE THE BODY BY MEANS OF ULTRASOUND

[75] Inventors: Helmut Wurster, Oberderdingen; Werner Krauss, Maulbronn, both of Fed. Rep. of Germany

[73] Assignee: Richard Wolf GmbH, Fed. Rep. of Germany

[21] Appl. No.: 155,149

[22] Filed: Feb. 11, 1988

[30] Foreign Application Priority Data

Feb. 17, 1987 [DE] Fed. Rep. of Germany ....... 3704909

[51] Int. Cl.$^5$ ............................................ A61B 17/22
[52] U.S. Cl. ............................ 120/660.03; 128/24 EL
[58] Field of Search ................ 128/328, 24 A, 24 EL, 128/660,03, 660.1, 660.09, 399; 606/127, 128

[56] References Cited

U.S. PATENT DOCUMENTS

| | | |
|---|---|---|
| 3,237,623 | 3/1966 | Gordon . |
| 3,338,235 | 8/1967 | Gordon . |
| 3,752,255 | 8/1973 | Hill et al. . |
| 3,927,661 | 12/1975 | Takemura . |
| 4,017,931 | 10/1986 | Rory .............. 128/328 X |
| 4,092,867 | 6/1978 | Matzuk . |
| 4,103,677 | 8/1978 | Lansiart et al. . |
| 4,151,834 | 5/1979 | Sato et al. .......... 128/660.1 |
| 4,159,462 | 6/1978 | Rocha et al. . |
| 4,206,653 | 6/1980 | Lemay . |
| 4,271,842 | 6/1981 | Specht et al. . |
| 4,455,872 | 6/1984 | Kossoff et al. ................ 128/660.09 |
| 4,526,168 | 7/1985 | Hassler et al. . |
| 4,541,435 | 9/1985 | Saito et al. . |
| 4,610,249 | 9/1986 | Makofski .......... 128/328 S |
| 4,620,545 | 11/1986 | Shene et al. . |
| 4,669,483 | 6/1987 | Hepp et al. ....... 128/328 S |
| 4,674,505 | 6/1987 | Pauli et al. . |
| 4,763,652 | 8/1988 | Brisson et al. .............. 128/328 S |
| 4,771,787 | 9/1988 | Wurster ............ 128/328 S |
| 4,787,394 | 11/1988 | Ogura ............. 128/660.03 |

FOREIGN PATENT DOCUMENTS

| | | |
|---|---|---|
| 168559 | 1/1986 | European Pat. Off. . |
| 225104 | 6/1987 | European Pat. Off. . |
| 3543867 | 6/1987 | Fed. Rep. of Germany ...... 128/328 |
| 2587493 | 3/1987 | France . |
| 998173 | 7/1965 | United Kingdom . |
| 2113099 | 8/1983 | United Kingdom . |

OTHER PUBLICATIONS

C. R. Hill, "Ultrasonic Imaging", Journal of Physics & Scientific Instruments, vol. 9, Mar., 1976.

Coleman, Lizzi and Jakobiec, "Therapeutic Ultrasound in the Production of Ocular Lesions", *American Journal of Opthalmology* 86:185–192, 1978.

Coleman, Lizzi, and El-Mofty, Driller and Franzen, "Ultrasonically Accelerated Resorption of Vitreous Membranes", *American Journal of Opthalmology,* 89: 490–499, 1980.

Coleman, Lizzi, Chang and Driller, "Applications of Therapeutic Ultrasound and Ophthalmology", *Progress in Medical Ultrasound,* vol. 2, 1981.

Lizzi, Coleman, Driller, Ostromogilsky, Chang and Greenall, "Ultrasonic Hyperthermia for Ophthalmic Therapy", IEEE Transactions on Sonics and Ultrasonics, vol. SU–31, No. 5, Sept., 1984.

*Primary Examiner*—Lee S. Cohen
*Assistant Examiner*—John D. Zele
*Attorney, Agent, or Firm*—Panitch Schwarze Jacobs & Nadel

[57] ABSTRACT

Apparatus for spatial location and destruction of an object inside a patient's body by means of ultrasound transmitted to the patient's body via a coupling fluid, the apparatus comprises a focusing transducer for generating the ultrasound piezoelectrically to destroy the object, at least two transmitting and receiving locating transducers for locating the object under visual observation, said at least two locating transducers being incorporated, installed or mounted in said focusing transducer and being operable to generate B-images which are displayed optionally individually and/or in combination as a spatial image on at least one monitor, there being preferably, three such locating transducers for generating the B-images.

15 Claims, 6 Drawing Sheets

APPARATUS FOR SPATIAL LOCATION AND DESTRUCTION OF OBJECTS INSIDE THE BODY BY MEANS OF ULTRASOUND

BACKGROUND OF THE INVENTION

1. Field of the Invention

The invention relates to apparatus for the spatial location and destruction of an object inside a patient's body by means of ultrasound which is transmitted to the patient's body via a coupling fluid, which is used for the destruction of the object, and which is generated piezoelectrically by means of a focusing transducer and wherein the focus of the transducer is aligned with the object under observation following location of the object by means of transmitting and receiving locating transducers.

2. Description of the Prior Art

The location of objects within a patient's body which are to be destroyed, such as stone concretions, tissue sections and the like, may be carried out under observation using X-ray or ultrasound technology. However, X-ray technology has particular disadvantages including exposure of the patient to radiation and unsuitability for performing simultaneous observation of the process of destruction of the object. The two locating techniques may obviously also be combined, for example by performing the continuous location and observation by means of ultrasound, and by checking the therapeutic results from time to time by means of X-rays. However, the provision of locating systems to perform this method would involve comparatively large expenditures. Accordingly, systems which use ultrasound only for locating the object and for checking on the therapeutic result obtained are more satisfactory. If the therapeutic ultrasound is generated by means of a cup or bowl shaped focusing transducer comprising a piezoelectric element or a mosaic of several piezoceramic elements, an ultrasonic B-scanner may be provided. Such a B-scanner can be arranged to scan a sector shaped field for example, at the center, coincident with the axis of the transducer cup or bowl, to produce a B-image. The focus of the focusing transducer is provided as a target mark on a monitor, so that it is possible to establish from the position of the object depicted by the B-image with respect to the target mark by what distance the focusing transducer should be displaced with respect to the patient in one plane or several planes so that the focus may finally be aligned precisely with the object. The locating action and alignment of the transducer may then also be performed in another plane, by turning the B-scanner through 90° for example. On the other hand, it is equally possible to operate with several locating transducers each of which transmits ultrasound waves. In such a case, the locating transducers also may simultaneously be positioned and arranged to receive the echo signals from these waves, unless it is preferred to receive the echo signals by means of separate ultrasound or pressure receivers.

However, problems arise with such location systems since, in certain disadvantageous positions of the locating, the effective transducer area can be masked by the locating transducers, causing a loss of active focusing transducer area. Furthermore, until now physicians did not have the means of establishing without difficulty the precise dimensions of an object. This is of importance to enable the physician even at the beginning of the treatment if possible, to determine the precise point at which the object (such as a kidney stone for example) should first and preferentially be bombarded with ultrasound to secure optimum results.

Accordingly, the main object of the present invention is to provide a structurally uncomplicated and highly efficient apparatus for spatial location and destruction of objects inside the body, which provides the physician with improved capabilities for locating and continuously monitoring the position as well as destruction of the object.

SUMMARY OF THE INVENTION

The present invention comprises in an apparatus for spatial location and destruction of an object inside a patient's body by means of ultrasound transmitted to the patient's body, via a coupling fluid, the apparatus comprising a focusing transducer for piezoelectrically generating ultrasound to destroy the object, at least two transmitting and receiving locating transducers for locating the object under observation, said atleast two locating transducers being incorporated or installed in said focusing transducer and being operable to generate B-images. Preferably, three locating transducers for generating B-images are installed in the focusing transducer.

Advantageously, the B-images may be displayed as a spatial image on a monitor, either individually and/or in combination.

To this end, the scan planes of the locating transducers which may, for example be, constructed as Bscanners may extend transversely to the symmetry axis of the therapeutic or focusing transducer and intersect the symmetry axis at the focus. On the other hand, the scan planes of the locating transducers may also intersect each other longitudinally on the symmetry axis of the transducer, that is to say in such manner that the symmetry axis lies in all the scan planes and the focus of the focusing transducer lies on the line of intersection of the scan planes. Both the previously referred to modes of operation of the B-scanners may also be obtained if the B-scanners or their transducer crystals are rotatable around their axes by a preset angle of 90°, so that they may jointly be shifted from one plane of operation to the other by equidirectional angular movement.

If three or more B-scanners are utilized, these scanners may then create a spatial "real-time" image of the object, especially if they can also be moved or wobbled through a small angle at right angles to their scan planes in a reciprocating manner, so that sector-like scanning of the target area will be achieved.

In order that the B-scanners do not affect each other in parallel operation, preferably drives for their scanner or transducer crystals are synchronised electrically and their electrical signals are called up consecutively. In this case, the drives constituted by motors for driving the crystals of the B-scanners in oscillation are synchronised with respect to their speed of turning movement or rotation and phase setting, the angular position of the motors being detected electronically and fed to a phase comparator circuit, so that the image display may be generated under synchronisation of the motors are the scanner crystals.

A spatial image may then be computed and displayed a monitor by means of an appropriate software program in a computer from the signals received from the B-scanners, so that the physician may perceive the precise dimensions of the object located and may thereupon decide which part of the object should first be acted upon by the therapeutic ultrasound.

On the other hand, the possibility also exists for the physician to allow the B-scanners to operate in series and for the B-images to be called up consecutively. In this case too, the physician may, in principle, obtain a spatial image of the object since he may arrange for the stored B-images to be displayed on a monitor in a specific sequence separately and if appropriate also in superimposition. However in such a case a "real-time" image will not always be obtained, if the object located should have changed its position because of any movement of the patient during the storing of the B-images.

The B-images are conveniently stored separately by scan planes and scanners in a storage matrix and are called up from the storage matrix for separate or combined spatial display on a monitor.

If a monitor is utilised having an image screen bearing the target mark of the transducer focus which is to be placed in coincidence with the object by displacement of the transducer, it is possible to proceed in such manner that the co-ordinates of the target mark are stored and that the object displayed in a respective plane on the image screen of the monitor is scanned by means of a light pen to allow feeding of the plane co-ordinates of the object as electrical signals into a computer. The latter has simultaneously fed to it the target mark coordinates allocated to the scan plane in question, in the form of other signals, so that the computer may compute the distance between the focus of the object from the said signalsand energize drive motors via a displacement software unit, which displace the transducer in at least one plane untilthe focus and the object are coincident.

The aforesaid computer or a separate computer may be provided, to which the image signals of the B-scanners are fed in series or in parallel, so that the computer processes these signals into a spatial image which may be displayed on a monitor. Regarding the image signals, the computer may to this end revert to stored signal data or to current scanner data which are obtained direct by means of the locating transducer without intermediate storage.

If the locating transducers are installed in the focusing transducer in such manner that the active surfaces of all the transducers extend flush in the bowl surface, this results in identical trajectories for the locating or diagnostic ultrasound and for the therapeutic ultrasound. Precise determination and destruction of the object are made possible thereby, in which refractions of the ultrasound are at least largely balanced or rendered noncritical by a multiscan system of this kind.

BRIEF DESCRIPTION OF THE DRAWINGS

In order that the invention may be more readily understood, reference will now be made, by way of example, to the accompanying drawings, in which.

DESCRIPTION OF THE PREFERRED EMBODIMENTS

Figure 1:
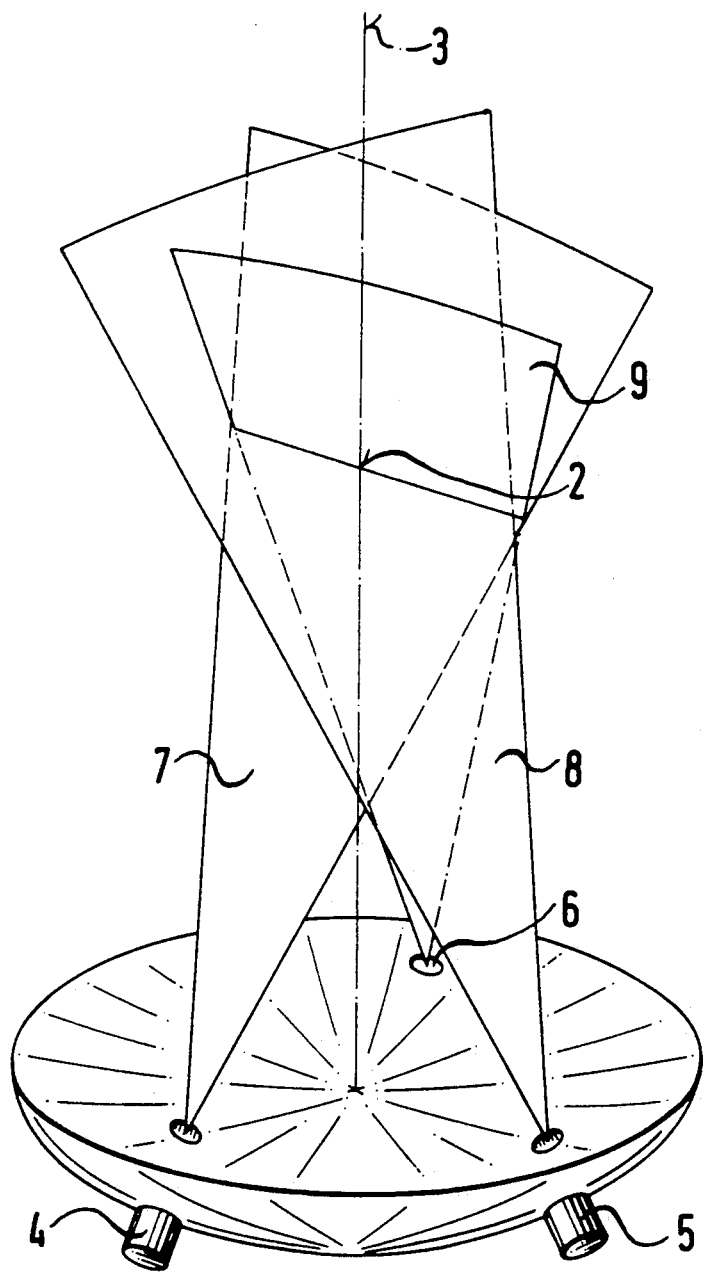
FIG. 1 is a diagrammatic perspective view from one side of a therapeutic focusing transducer including three locating transducers and forming part of an apparatus for the spatial location and destruction of an object inside a patient's body by means of ultrasound.
Figure 2:
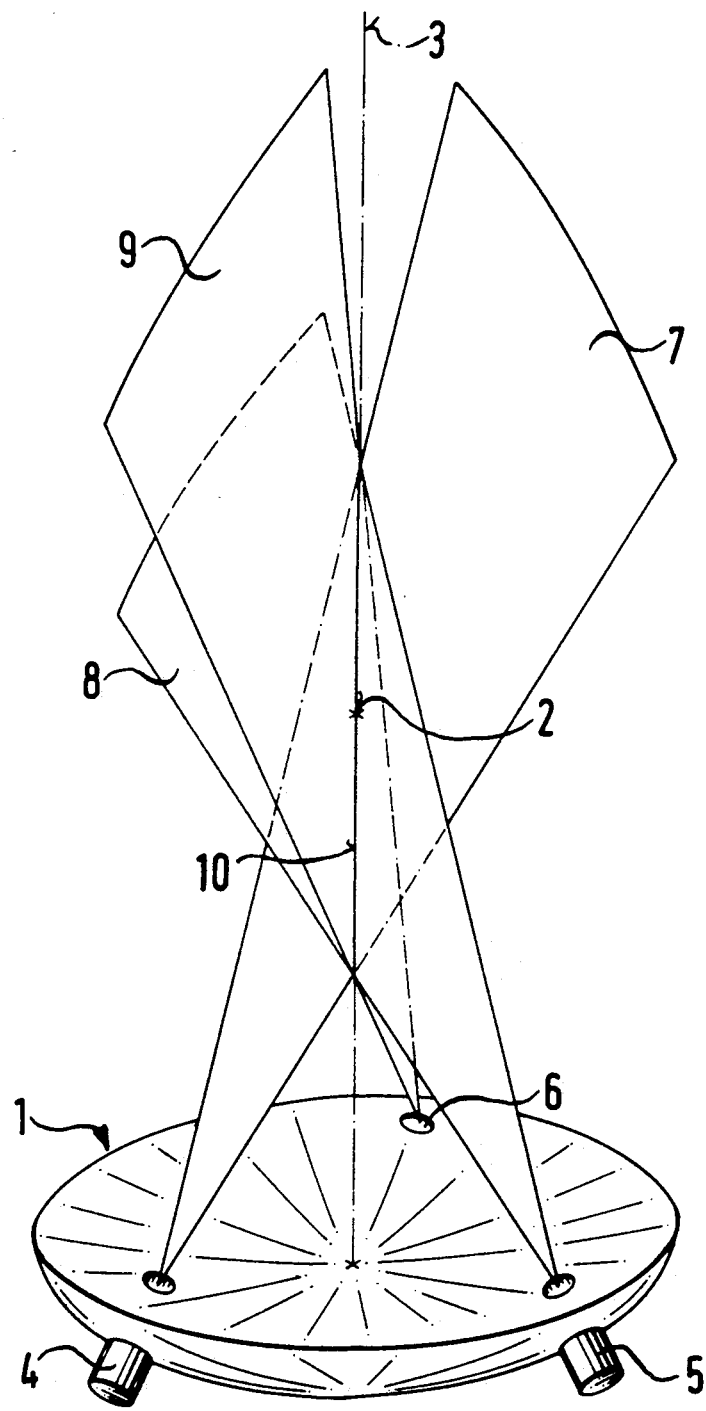
FIG. 2 is a view similar to that of FIG. 1, in which the locating transducers operate in scan planes different from those shown in FIG. 1.
Figure 8:
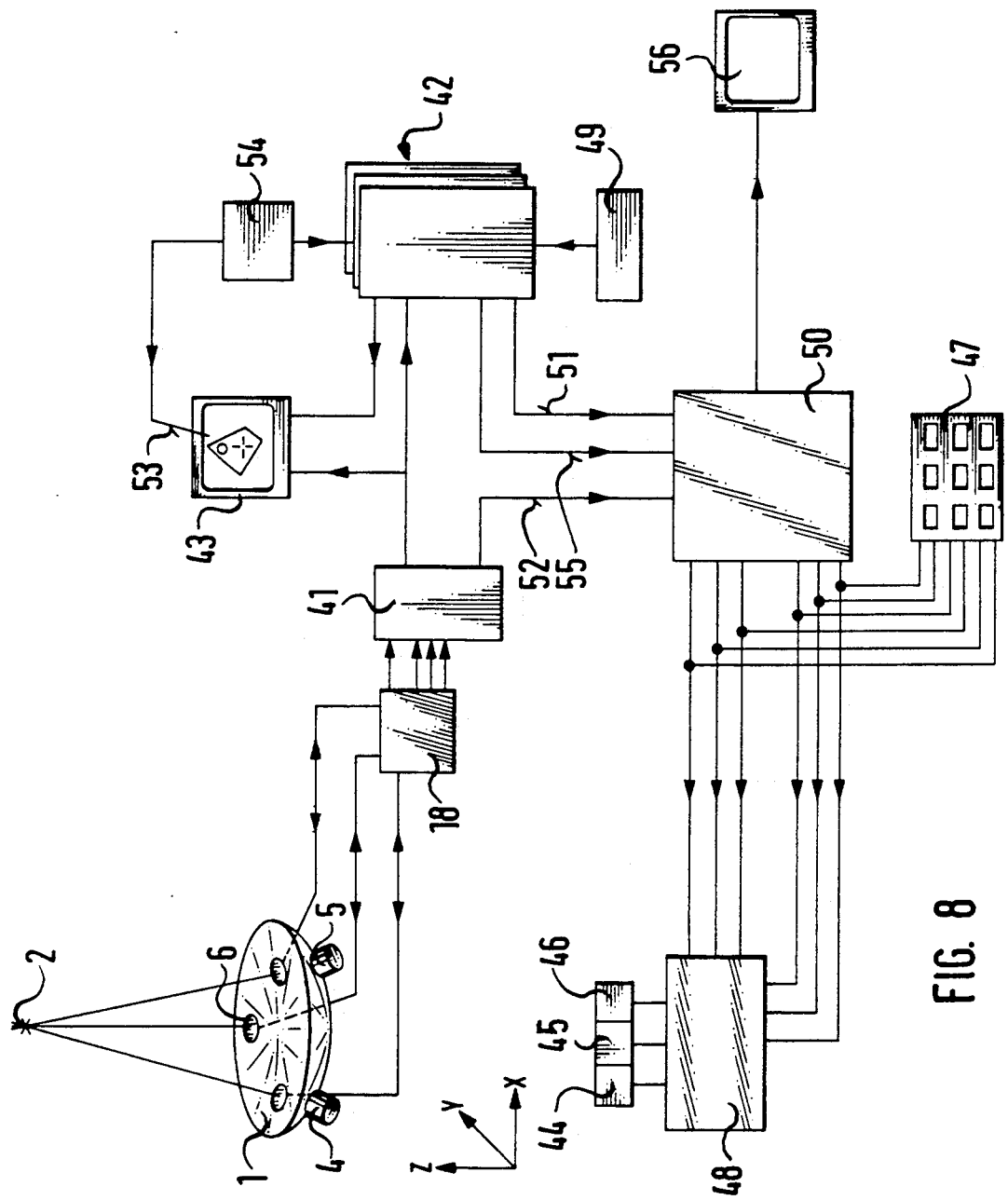
FIG. 8 is a block diagram of the apparatus for the spatial location and destruction of an object inside a patient's body by means of ultrasound and constructed according to the invention.

Referring to FIGS. 1, 2 and 8 of the drawings, there is shown the transducer 1 for generating and focusing therapeutic ultrasound and having the shape of a spheroidal bowl which has a concave surface presented by a mosaic of piezoelectric elements. The ultrasound waves generated by the transducer 1 converge at the focus 2 on the transducer central axis or axis of symmetry 3. The ultrasound waves are transmitted in conventional manner via a coupling fluid (not shown) to the patient's body and ultimately to the object which is to be destroyed. The structure, function and also the various possible ways for providing motorized displacement of the transducer 1 along x, y and z co-ordinates are common knowledge and consequently need not be illustrated and described further.

Three B-scanners 4, 5 and 6 are installed or mounted as locating transducers in the transducer 1 of FIGS. 1, 2 and 8 with their oscillatingly or pivotally driven transducer crystals situated in the same plane as the adjacent piezoelectric elements of the transducer 1 i.e. the exposed surfaces of the B-scanner transducer crystals are coincident with the concave surface of the transducer 1 and this in such manner that according to FIG. 1, the scan planes 7, 8 and 9 of the transducers 4, 5 and 6 respectively extend or rather oscillate transversely to the axis 3 and intersect the axis 3 at the focus 2.

On the other hand, it is also possible to proceed in such manner according to FIG. 2 that the scan planes of the B-scanners 4, 5 and 6 intersect each other longitudinally along the axis 3 of the transducer 1 in such manner that the axis lies in all the scan planes, and the focus 2 of the transducer lies on the line of intersection 10 of the scan planes.

The B-scanners 4, 5 and 6 or rather their transducer crystals may be turned around their longitudinal axes by means of respective electric motors which, as shown in FIGS. 1 and 2, are in the form of cylindrical elements that project outwardly and downwardly from the transducer 1. For example if the B-scanners are turned from their positions in which the scan planes are as shown in FIG. 1 to the other positions in which the scan planes are as shown FIG. 2, they will have been turned through 90°. The possibility also exists moreover to wobble the B-scanners at right angles to, and out of their corresponding scan planes, through a small angle of the order of magnitude of say 2° to 3° to obtain a sector like scanning of the target area. A spatial scan of this target area is obtained with at least three or more B-scanners, although a spatial scan can also be obtained with two B-scanners which are rotatable around their longitudinal axes by respective electric motors.

The B-scanners 4, 5 and 6 may be switched to transmission and reception consecutively in chronological sequence, so that one B-scanner only and then the next one is in operation to produce a scan line, and the scan lines of all the B-scanners are interimbricated in comb-like fashion as considered chronologically and geometrically. In this manner, the B-scanners will not obstruct each other in the case of a parallel image integration, since each scanner receives no more than the echo signal generated on the basis of its own transmission pulse.

Figure 3:
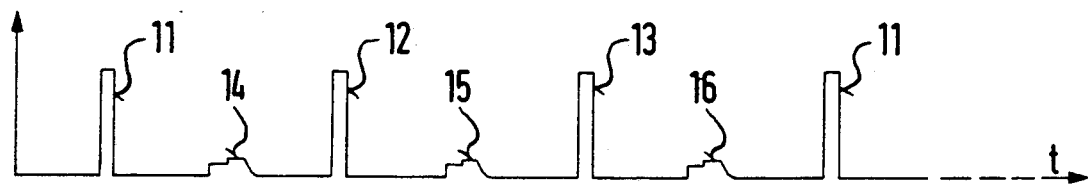
FIG. 3 shows a succession of transmission and reception pulses during operation in parallel of the locating transducers.

FIG. 3 shows how these signals appear in preset succession and in respect of the time axis t. The pulses 11, 12 and 13 are thus the individual transmission pulses and the pulses 14, 15 and 16 are the individual reception pulses of the three B-scanners. This means that, for example the B-scanner 4 initially transmits the pulse 11 and receives the pulse 14, the B-scanner 5 then transmits the pulse 12 and receives the pulse 15, etc., until the B-scanner 4 is reached again in turn. In this manner, all the B-scanners may transmit and receive approximately 150 to 200 pulses during each pivotal displacement of their transmitting and receiving transducer crystal, so that a corresponding number of scan lines is produced, which when combined form the scan planes 7, 8 and 9 which actually have the shape of a scan line fan.

Figure 4:
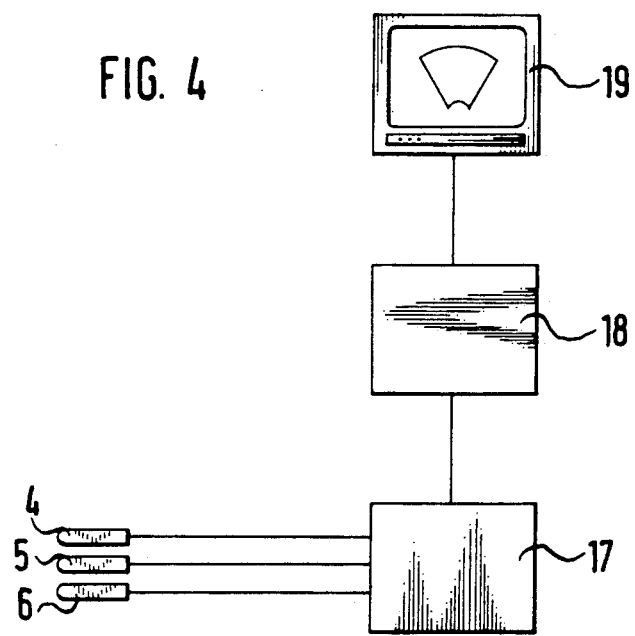
FIG. 4 is a block circuit diagram showing the locating transducer coupled to an ultrasound device.

The transducer 1 and the B-scanners 4, 5 and 6 are operated by ultrasound devices. The ultrasound device (not shown) for the transducer 1 is obviously designed for a correspondingly greater transmission and reception performance, than the B-scanners which operate at lesser power. So that a respective ultrasound device need not be provided for each B-scanner, then as shown in FIG. 4, all three B-scanners, 4, 5 and 6 may be switched one after the other via an interface 17 to a single and commercially available ultrasound device 18. The interface 17 controls the chronological sequence of the operation of the B-scanners via the ultrasound device 18, so that their signals produce the pulse sequence shown in FIG. 3. Moreover, the interface also transmits the reception pulses of the B-scanners to a monitor 19 for display of the B-images, that is to say via other parts of the apparatus which will be hereinafter described.

Figure 5:
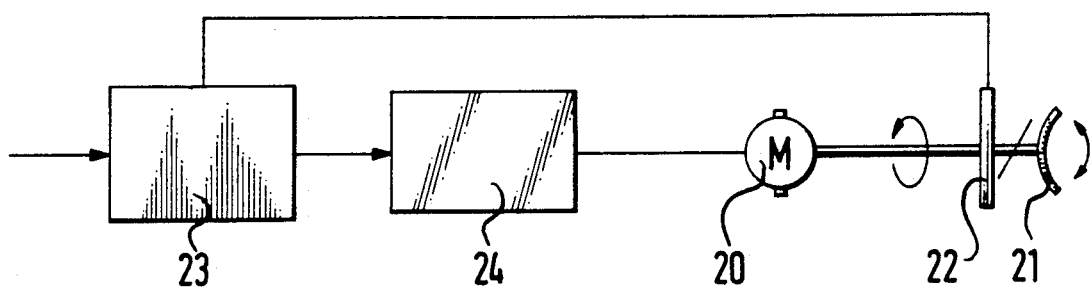
FIG. 5 is a block circuit diagram showing the drive for one B-scanner motor.

Referring now to FIG. 5, this shows a driving motor 20 which is operative to cause the crystal 21 of one of the B-scanners 4, 5 or 6 to move with an oscillatory or pivoting scanning motion, by the rotary movement of the motors being converted into the required scanning motion by means of a mechanism which is well known and will, therefore, not be further described. The motor 20 should have a specific phase setting and speed of rotation which is detected by means of an incremental emitter 22 and fed to a phase lock loop circuit 23. This compares the actual value of the speed of rotation with a preset scheduled value and continues to adjust the speed of rotation via the motor feed unit 24 until the motor has reached the preset speed of rotation. All the drive motors for the B-scanners are operated in a corresponding way.

Figure 6:
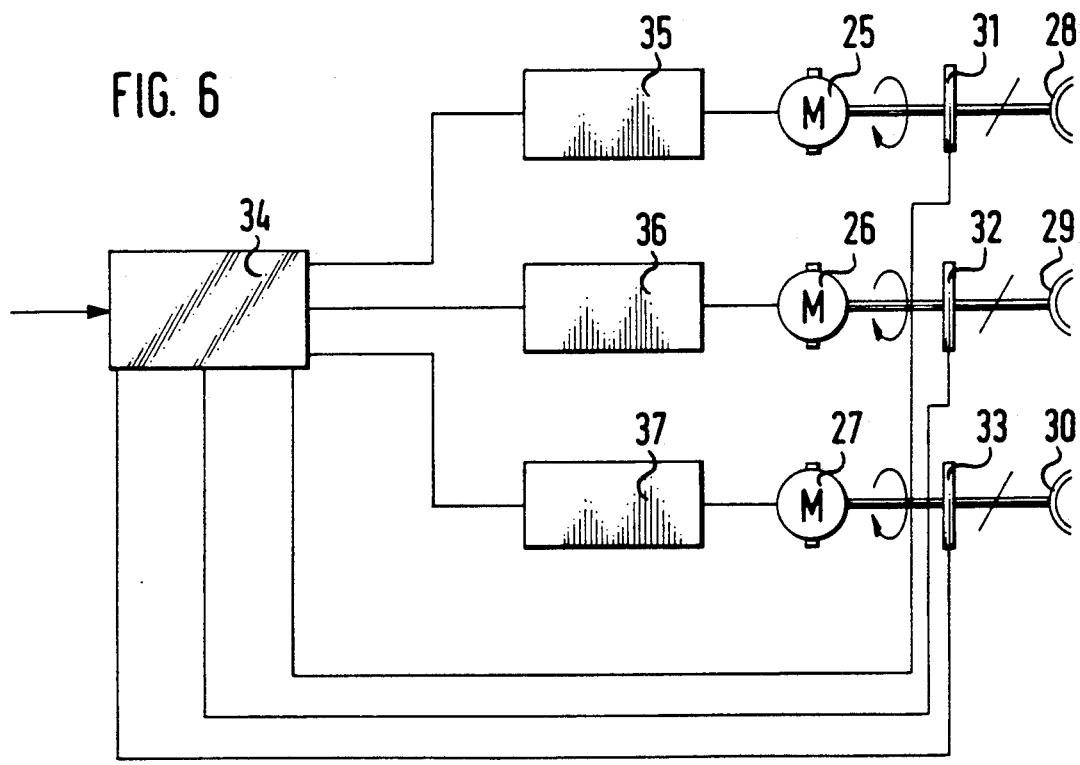
FIG. 6 is a block circuit diagram showing the drive for three B-scanner motors.

Furthermore, the drive motors for the B-scanners are synchronised not only with respect to their rotational speeds but also with respect to their phase setting, so that all the scanner crystals oscillate synchronously and equidirectionally. Thus, in FIG. 6, there are three stepping drive motors 25, 26 and 27 for the crystals 28, 29 and 30 respectively of the three B-scanners 4, 5 and 6. Incremental emitters 31, 32 and 33 detect the instantaneous rotary position or phase setting of the drive motors and feed their signals to a phase comparator circuit 34, in which these signals are compared to a scheduled value and which controls the generators 35, 36 and 37 in such manner that the motors are governed at a coincident phase setting.

Instead of the B-scanners or sector scanners for producing B-images already described, other image-generating systems may be used, such as for example piezoelectric elements arranged in intersecting rows in the transducer bowl, which are operated as transmitters and receivers and may generate B-images.

Figure 7:
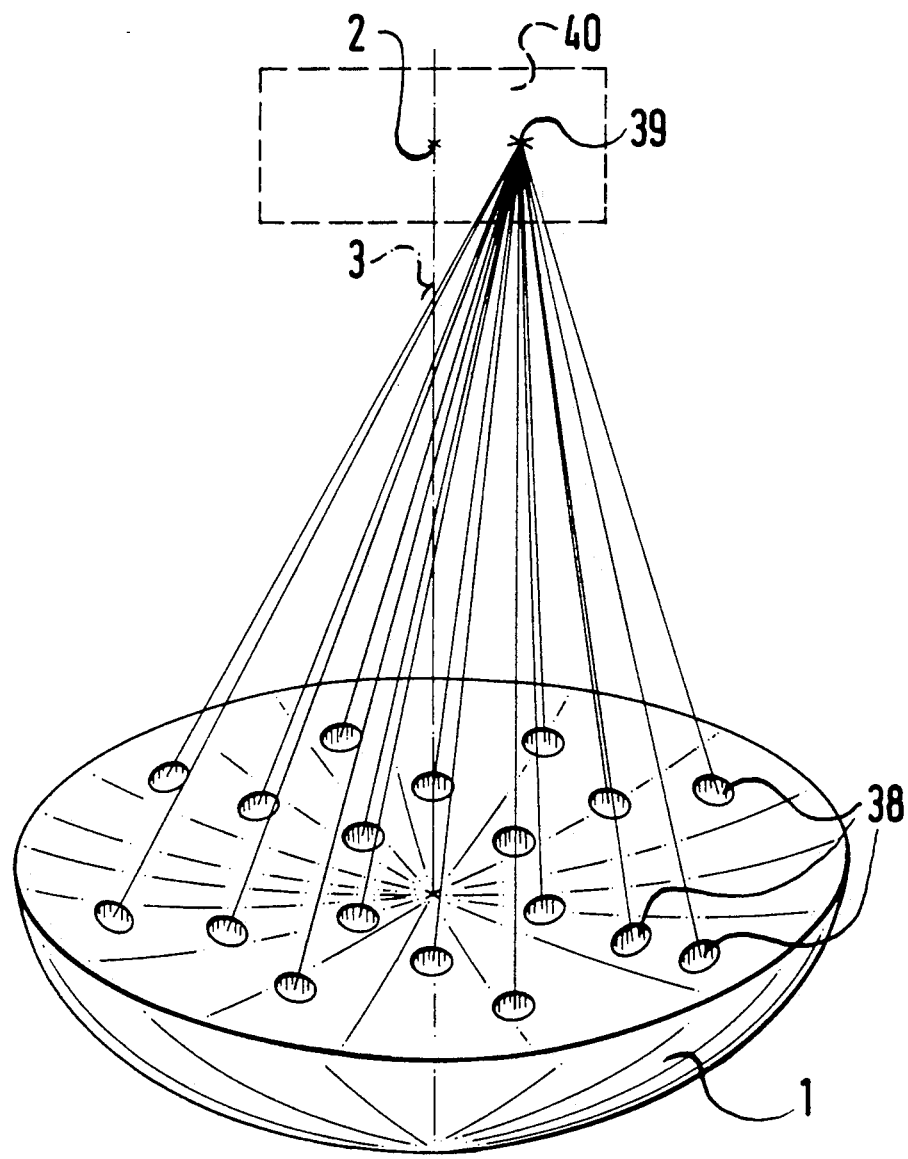
FIG. 7 shows an arrangement of a locating transducer operated in the manner of a phased array.

Another way of producing B-images is by means of so-called phased arrays as shown in FIG. 7, in which individual piezoelectric elements 38 are distributed within the transducer bowl 1 and which may be energised in staggered chronological sequence so that the sound beams of the elements in each case coincide at the image dot 39 which is to be depicted. To this end, the energizing power is so selected from pulse to pulse that the image dot 39 moves in a plane 40 in which the focal point 2 of the transducer 1 is located and a two-dimensional B-image is generated. The image dot 39 may also be allowed to move successively in several image planes or to jump from image plane to image plane, so that a spatial illustration of the target area may thus be obtained by means of a computer which evaluates the reception signals either in series operation or parallel operation for the scan planes selected and causes these to be displayed on a visual monitor.

Referring now to FIG. 8, the B-scanners 4, 5 and 6 are operated as previously described via the ultrasound device 18. The scanner data is fed via a control system 41 to a storage matrix 42 which in this case comprises three memories corresponding to the number of B-scanners. In the respective memories the data of the B-images are stored separately according to scanners and scan planes and may be called up for display of the individual B-images on the monitor 43. Visual display on the image screen of the monitor 43 shows a sector-shaped scan plane, the target mark denoted by a cross and corresponding to the focus 2 of the transducer 1, and the object to be destroyed denoted by a circle. By reference to this display, a physician may now determine the direction in which the transducer 1 should be displaced mechanically by motors 44, 45 and 46 in the directions of the co-ordinates x, y or z to bring the target mark and the object into coincidence with a particular scan plane. The physician may perform this displacement, e.g. by means of a manual control system 47 which transmits appropriate control pulses to the servo motors 44, 45 and 46, via a displacement software unit 48.

After the transducer focus has thus been aimed at the object, for example in the x, y plane, alignment in another plane may be performed subsequently, after the corresponding B-image has been called up from the storage matrix 42 and displayed on the monitor 43. It is not absolutely necessary however to operate with stored B-images, since it is also perfectly possible to feed the actual scan data direct to the monitor 43 by means of the control system 41 while by-passing the storage matrix 42.

Furthermore, the co-ordinates of the target mark may also be stored in the storage matrix 42 as the instantaneous position of the transducer focus. By means of a feed device 49, the target mark data may be fed to a computer 50 via a conductor 51, and the actual scanner data may also be fed to the computer 50 via another conductor 52. The computer 50 may then perform a calculation for one scan plane or if applicable in parallel for several scan lines, of the distances by which the transducer 1 should be displaced by the motors 44, 45 and 46 to align the focus 2 on the object which is to be destroyed. To this end, the computer 50 will feed the distance value in the form of electrical signals to the displacement software unit 48, which reaches a decision based on the decisive scan planes and their position, regarding the particular motor 44, 45 or 46 which is to be operated to displace the transducer 1. To this end, a check may also be made currently on the displacement motion by observing the travel of the object on the monitor 43.

The object depicted on the image screen of the monitor 43 may also be scanned manually by means of a light pen 53, so that the plane co-ordinates of the object may be fed into the storage matrix via the control system 54, so that the data of the target mark coordinates may be called up by the computer 50 from the storage matrix via the conductor 51, and the data of the object coordinates may also be called up via the conductor 55, and the distances may be calculated from these by which the transducer 1 should be displaced in one or more planes to coincide the focus 2 finally with the object. Furthermore, it is also possible in this case to feed the object co-ordinates determined by means of the light pen 53 directly into the computer 50 while by-passing the storage matrix 42.

The computer 50 may finally calculate a spatial image from the B-image signals fed to it serially and successively by scan planes in parallel from all scan planes, which is appropriately caused to be displayed on the image screen of another monitor 56, so that the physician has the possibility to observe and assess the illustration of the scan planes or individual images on the monitor 43 and the composite spatial or perspective image on the monitor 56.

It should be appreciated that the invention is not restricted to the embodiments described but includes all modifications and variations falling within its scope.

What is claimed is:

1. In an apparatus for destruction of an object inside a patient's body by means of ultrasound, of the type comprising a piezoelectric focusing transducer for generating ultrasound energy to destroy the object, and improvement for aligning the focusing transducer with the object comprising:
   at least two ultrasonic locating transducers; and
   means for mounting the at least two locating transducers remotely positioned from each other within said focusing transducer for generating ultrasound pressure waves along separate axes.

2. The invention of claim 1 wherein the focusing transducer defines a cup-shaped transducer surface, wherein the transducer surface defines a plurality of openings, and wherein each of the locating transducers is positioned in a respective one of the openings.

3. The invention of claim 1 wherein each of said locating transducers comprise means for generating B-scanner data.

4. The invention of claim 3 further comprising a monitor and means for displaying on the monitor an image comprising information from at least one of said means for generating B-scanner data.

5. The invention of claim 3 further comprising:
   a monitor; and
   storage matrix means coupled with the monitor for storing the B-scanner data separately by scan plane and locating transducer for subsequent retrieval for spatial display on the monitor.

6. The invention of claim 5 further comprising:
   means for displaying on the monitor a target mark having target mark coordinates which indicate a focus of the focusing transducer;
   means for generating object coordinates of the object to be destroyed;
   means, responsive to the target mark coordinates and the object coordinates, for generating control signals adapted to bring the target mark coordinates into coincidence with the object coordinates; and
   means, responsive to the control signals, for moving the focusing transducer to bring the focus into coincidence with the object.

7. The invention of claim 1 wherein said at least two locating transducers comprises three locating transducers.

8. The invention of claim 1 wherein said focusing transducer defines a focus and an axis of symmetry, wherein the locating transducers define respective scan planes, and wherein the symmetry axis extends transversely through each of the scan planes and the scan planes intersect the symmetry axis at the focus of the focusing transducer.

9. The invention of claim 1 wherein said focusing transducer defines a focus and an axis of symmetry, wherein the locating transducers define respective scan planes, and wherein the scan planes intersect each other along a line that includes the symmetry axis such that the symmetry axis lies in all of the scan planes, and the focus of the focusing transducer lies on the line of intersection of the scan planes.

10. The invention of claim 1 wherein each of the locating transducers comprises a respective B-scanner, each B-scanner comprising a respective transducer crystal and means for moving the transducer crystal through a preset angle around a respective scan axis.

11. The invention of claim 1 wherein each of the locating transducers comprises a respective B-scanner, and wherein the invention further comprises means for successively switching the B-scanners between transmission and reception, such that no more than one of the B-scanners is in operation at any time for generation of a scan line, and the scan lines of each of the B-scanners are interposed in time between scan lines of the other B-scanners.

12. The invention of claim 1 wherein each of the locating transducers comprises a respective B-scanner, and wherein the invention further comprises an ultrasound means for operating the at lest two B-scanners and interface means connected between the ultrasound means and the at least two Bscanners for successively switching the at least two B-scanners to the ultrasound means and for controlling the chronological sequence of operation of the at least two Bscanners by the ultrasound means.

13. The invention of claim 1 each of the locating transducers comprises a respective B-scanner, each B-scanner comprising:
   a transducer crystal, and
   a motor coupled to the crystal to pivot the crystal.

14. The invention of claim 13 wherein each said B-scanner further comprises:
   means for detecting rotational positions of the motor; and further comprising
   a phase comparator circuit coupled to each of the detecting means and the motors to synchronize the motors.

15. The invention of claim 1 wherein each of the locating transducers comprises a respective B-scanner which generates an B-scanner data signal, and wherein the invention further comprises means for processing the B-scanner data to generate a signal for display on a monitor.

* * * * *